United States Patent
Ogawa et al.

(10) Patent No.: US 6,831,092 B1
(45) Date of Patent: Dec. 14, 2004

(54) PESTICIDAL COMPOSITION AND METHOD FOR CONTROLLING PESTS

(75) Inventors: Munekazu Ogawa, Shiga (JP); Akihiro Nishimura, Shiga (JP)

(73) Assignee: Ishihara Sangyo Kaisha, Ltd., Osaka (JP)

(*) Notice: Subject to any disclaimer, the term of this patent is extended or adjusted under 35 U.S.C. 154(b) by 0 days.

(21) Appl. No.: 10/030,685

(22) PCT Filed: Jul. 14, 2000

(86) PCT No.: PCT/JP00/04760

§ 371 (c)(1),
(2), (4) Date: Feb. 20, 2003

(87) PCT Pub. No.: WO01/05231

PCT Pub. Date: Jan. 25, 2001

(30) Foreign Application Priority Data

Jul. 16, 1999 (JP) .................................. 11-202874

(51) Int. Cl.[7] ................................ A01N 43/50
(52) U.S. Cl. ................ 514/398; 424/405; 424/406; 504/266; 504/277; 504/303; 504/336; 514/370; 514/478; 514/479; 514/617
(58) Field of Search ................ 424/405, 406; 514/227.8, 365, 370, 385, 398, 386, 476, 613, 617; 504/336, 266, 303, 277

(56) References Cited

U.S. PATENT DOCUMENTS 4,995,898 A * 2/1991 Nasu et al. .................. 71/90

FOREIGN PATENT DOCUMENTS

| EP | 0 639 574 | | 2/1995 |
|---|---|---|---|
| EP | 0 753 258 | | 1/1997 |
| JP | 0-301103 | * | 1/1991 |
| JP | 04 154704 | | 5/1992 |
| JP | 4-154704 | * | 5/1992 |
| WO | 96 03044 | | 2/1996 |
| WO | 99 11125 | | 3/1999 |
| WO | 99 27788 | | 6/1999 |

* cited by examiner

Primary Examiner—Neil S. Levy
(74) Attorney, Agent, or Firm—Oblon, Spivak, McClelland, Maier & Neustadt, P.C.

(57) ABSTRACT

A pesticidal composition comprising at least one specific imidazole and at least one fungicide selected from the group consisting of (S)-5-methyl-2-methylthio-5-phenyl-3-phenylamino-3,5-dihydroimidazole-4-one, isopropyl 2-methyl-1-[(1-p-tolylethyl)carbamoyl]-(S)-propylcarbamate, 3,5-dichloro-N-(3-chloro-1-ethyl-1-methyl-2-oxopropyl)-4-methyl-benzamide and N-(α-cyano-2-thienyl)-4-ethyl-2-(ethylamino)-5-thiazole carboxyamide, as active ingredients.

7 Claims, No Drawings

PESTICIDAL COMPOSITION AND METHOD FOR CONTROLLING PESTS

TECHNICAL FIELD

The present invention relates to a pesticidal composition useful as an agricultural and horticultural pesticide having a pesticidal effect, particularly an exceptionally improved effect of preventing and/or curing plant diseases, and a method for controlling pests by using said composition.

BACKGROUND ART

JP-A-1-131163 discloses that imidazole compounds to be used as an active ingredient for the pesticidal composition of the present invention are useful as pesticides, and that they can be used together with other fungicides as the case requires. Further, as mixed pesticidal compositions containing the above imidazole compounds as active ingredients, ones as disclosed in JP-A-11-71209, JP-A-11-106301 and JP-A-11-124305, may be mentioned. Further, WO99/27788 discloses a possible combination of the compound No. 1 as described hereinafter and (S)-5-methyl-2-methylthio-5-phenyl-3-phenylamino-3,5-dihydroimidazole-4-one. However, it has not been known that a pesticidal composition comprising the above imidazole compound and at least one fungicide selected from the group consisting of (S)-5-methyl-2-methylthio-5-phenyl-3-phenylamino-3,5-dihydroimidazole-4-one, isopropyl 2-methyl-1-[(1-p-tolylethyl)carbamoyl]-(S)-propylcarbamate, 3,5-dichloro-N-(3-chloro-1-ethyl-1-methyl-2-oxopropyl)-4-methylbenzamide and N-(α-cyano-2-thienyl)-4-ethyl-2-(ethylamino)-5-thiazole carboxyamide, has a distinguished pesticidal effect.

With respect to the pesticidal effect of each imidazole compound of the formula (I) as described hereinafter, its effect may be insufficient against certain specific pests, or the residual effect will last only for a relatively short period of time, so that the pesticidal effect against pests tends to be practically insufficient in some cases.

DISCLOSURE OF THE INVENTION

The present inventors have conducted extensive studies to overcome the above problems and as a result, have found that when the imidazole compound of the formula (I) as described hereinafter is used together with at least one fungicide selected from the group consisting of (S)-5-methyl-2-methylthio-5-phenyl-3-phenylamino-3,5-dihydroimidazole-4-one, isopropyl 2-methyl-1-[(1-p-tolylethyl)carbamoyl]-(S)-propylcarbamate, 3,5-dichloro-N-(3-chloro-1-ethyl-1-methyl-2-oxopropyl)-4-methylbenzamide and N-(α-cyano-2-thienyl)-4-ethyl-2-(ethylamino)-S-thiazole carboxyamide, an excellent pesticidal effect can be obtained, which is unexpected from a single use of each compound alone. The present invention has been accomplished on the basis of this discovery.

Namely, the present invention relates to a pesticidal composition comprising at least one imidazole compound of the formula (I):

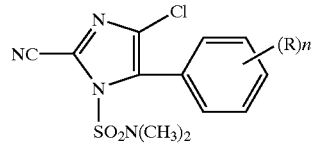

formula (I)

wherein R is a lower alkyl group or a lower alkoxy group, and n is an integer of from 1 to 5, and at least one fungicide selected from the group consisting of (S)—S-methyl-2-methylthio-S-phenyl-3-phenylamino-3,5-dihydroimidazole-4-one, isopropyl 2-methyl-1-[(1-p-tolylethyl)carbamoyl]-(S)-propylcarbamate. 3,5-dichloro-N-(3-chloro-1-ethyl-1-methyl-2-oxopropyl)-4-methylbenzamide and N-(α-cyano-2-thienyl)-4-ethyl-2-(ethylamino)-5-thiazole carboxyamide, as active ingredients.

In the imidazole compound of the formula (r), as the alkyl moiety in the lower alkyl group or the lower alkoxy group as defined by R, $C_{1-6}$ alkyl such as methyl, ethyl, propyl, butyl, pentyl or hexyl may be mentioned, and they may be linear or branched. Further, in the case where n is at least 2, the plurality of R may be the same or different.

Examples of the imidazole compound of the formula (I) include the following compounds:
4-chloro-2-cyano-1-dimethylsulfamoyl-5-(4-methylphenyl) imidazole (compound No. 1)
4-chloro-2-cyano-1-dimethylsulfamoyl-5-(4-methoxyphenyl)imidazole (compound No. 2)
4-chloro-2-cyano-1-dimethylsulfamoyl-S-(4-ethylphenyl) imidazole (compound No. 3), and
4-chloro-2-cyano-1-dimethylsulfamoyl-5-(3-methyl-4-methoxyphenyl)imidazole (compound No. 4)

Here, the imidazole compound of the above formula (I) may be produced by a method as disclosed in JP-A-1-131163 or EP-A-705823.

The above (S)-5-methyl-2-methylthio-5-phenyl-3-phenylamino-3.5-dihydroimidazole-4-one (hereinafter referred to simply as compound a) is a compound as disclosed in THE 1998 BRIGHTON CONFERENCE-Pests & Diseases P.319–326. The above isopropyl 2-methyl-1-((1-p-tolylethyl)carbamoyl)-(S)-propylcarbamate (hereinafter referred to simply as compound b) is a compound as disclosed in THE 1998 BRIGHTON CONFERENCE-Pests & Diseases P.367–374. 3.5-dichloro-N-(3-chloro-1-ethyl-1-methyl-2-oxopropyl)-4-methylbenzamide (hereinafter referred to simply as compound Q) is a compound as disclosed in THE 1998 BRIGHTON CONFERENCE-Pests & Diseases P.335–342. N-(a-cyano-2-thienyl)-4-ethyl-2-(ethylamino)-5-thiazole carboxyamide (hereinafter referred to simply as compound d) is a compound as disclosed in AG CHEM NEW COMPOUND REVIEW VOLUME17 1999, p.53. The above compounds a, a, C and d are fungicides having a preventive effect and a curative effect.

The pesticidal composition comprising as active ingredients at least one imidazole compound of the above formula (I) and at least one fungicide selected from the group consisting of the compounds a, b, c and d, exhibits an excellent fungicidal effect when applied to cultivated crop plants which are infected or are suspected of being infected with noxious fungi, including vegetables such as cucumber (*Cucumis sativus*), tomato (*Lycopersicon esculentum*) and eggplant (*Solanum melongena*), creal crops such as rice (*Oraza sativa*) and barley (*Hordeum vulgare*), beans (Legume), fruit trees such as apple (*Malus pumila*), pear (*Pyrus serotina, Pyrus ussuriensis, Pyrus communis*), grape (*Vitis vinifera*) and citrus (Citrus), and potato (*Solanum* tuberosum). Said composition is suitable for controlling diseases such as powdery mildew, downy mildew, *anthracnose*, gray mold, common green mold, scab, *Alternaria* blotch, bacterial blotch, purple blotch, melanose, late rot, late blight, early blight, rice blast, sheath blight, seedling damping-off and southern blight. Further, said composition exhibits an excellent effect of controlling soil-borne diseases caused by phytopathogenic fungi such as *Fusarium, Rhizoctonia, Verticillium, Plasmodiophora* and *Pythium*. The pesticidal composition of the present invention exhibits a long-term residual effect and a preventive and/or curative effect, and it is particularly excellent in preventive effect.

Specifically, the pesticidal composition of the present invention exhibits an excellent effect of controlling rice blast; rice sheath blight; cucumber *anthracnose*; downy mildew of cucumber, melon (*Cucumis melo*), cabbage (*Brassica*), Chinese cabbage (*Brassica*), onion (*Allium cepa*), pumpkin (*Cucurbita*) and grape; powdery mildew of wheat (*Triticum vulgare*), barley (*Hordeum vulgare*) and cucumber: late blight of potato, red pepper (*Capsicum annuum*), sweet pepper (*Capsicum annuum*), watermelon (*Citrullus vulgaris*), pumpkin, tobacco (*Nicotiana tabacum*) and tomato; wheat *Septria* disease; tomato early blight; citrus melanose; citrus common green mold; pear scab; apple *Alternaria* blotch; onion white late blight; watermelon brown rot; diseases such as gray mold, *Sclerotinia* rot, rust and bacterial blotch of various crops; and diseases by Phycomycetes such as soil-borne diseases caused by phytopathogenic fungi such as *Fusarium, Pythium, Rhizoctonia* and *Verticillium*. Further, said composition exhibits an excellent effect of controlling diseases caused by *Plasmodiophora*. More specifically, said composition exhibits a particularly excellent effect of controlling disease such as late blight of potato, red pepper, sweet pepper, watermelon, pumpkin, tobacco and tomato; and downy mildew of cucumber, melon, cabbage, Chinese cabbage, onion, pumpkin and grape.

The pesticidal composition of the present invention further exhibits an excellent effect of controlling agriculturally and horticulturally noxious insects, mites and nematodes, for example, insects such as planthoppers (*Delphacidae*), diamondback moth (*Plutella xylostella*), green rice leafhopper (*Nephotettix cincticeps*), adzuki bean weevil (*Callosobruchus chinensis*), common cutworm (*Spodoptera litura*) and grean peach aphid (*Myzus persicae*), mites such as twospotted spider mite (*Tetranychus urticae*), carmine spider mite (*Tetranychus cinnabarinus*) and citrus red mite (*Panonychus citri*), and nematodes such as southern root-knot nematoda (*Meloidogyne incognita*).

The plurality of active ingredients constituting the pesticidal composition of the present invention may be used in combination with an adjuvant to prepare various formulations such as an emulsifiable concentrate, a dust, a wettable powder, an aqueous solution, granules and a suspension concentrate, in the same manner as conventional agricultural chemical formulations. In this case, the compound of the above formula (I) and other specific compound may be mixed and prepared together, or they may be prepared separately and the resulting preparations may be mixed. These formulations can be practically used either as such or after diluted with a diluent such as water to a predetermined concentration. As the adjuvant, carriers, emulsifiers, suspending agents, thickeners, stabilizers, dispersants, spreaders, wetting agents, penetrating agents, antifreezing agents and antifoaming agents may, for example, be mentioned. They may be added optionally as the case requires. The carriers are classified into solid carriers and liquid carriers. Examples of the solid carriers include powders of animal and plant origin, such as starch, sugar, cellulose powder, cyclodextrin, activated carbon, soybean flour, wheat flour, rice hull powder, wood powder, fish powder and powdered milk: and mineral powders such as talc, kaoline, bentonite, organic bentonite, calcium carbonate, calcium sulfate, sodium bicarbonate, zeolite, diatomaceous earth, white carbon, clay, alumina, silica, sulfur powder and hydrated lime. Examples of the liquid carriers include water; vegetable oil such as soybean oil and cottonseed oil: animal oil such as beef tallow and whale oil; alcohols such as ethyl alcohol and ethylene glycol: ketones such as acetone, methyl ethyl ketone, methyl isobutyl ketone and isophorone; ethers such as dioxane and tetrahydrofuran; aliphatic hydrocarbons such as kerosine, coal oil and liquid paraffin; aromatic hydrocarbons such as toluene, xylene, trimethylbenzene, tetramethylbenzene, cyclohexane and solvent naphtha; halogenated hydrocarbons such as chloroform and chlorobenzene; acid amides such as dimethylformamide; esters such as ethyl acetate and fatty acid glycerin esters; nitriles such as acetonitrile, sulfur-containing compounds such as dimethyl sulfoxide, and N-methyl-2-pyrrolidone and N,N-dimethylformamide. Examples of the spreaders include sodium alkylsulfate, sodium alkylbenzenesulfonate, sodium lignin sulfonate, polyoxyethylene glycol alkyl ether, polyoxyethylene lauryl ether, polyoxyethylene alkyl aryl ether and polyoxyethylene sorbitan fatty acid ester.

In the pesticidal composition of the present invention, the suitable blending weight ratio of said at least one compound of the formula (I) to said at least one fungicide selected from the group consisting of the compounds a, b, c and d, is generally from 1:10000 to 10000:1, preferably from 1:1000 to 10000:1, more preferably from 1:200 to 200:1. Further, the most preferred blending weight ratio of said at least one compound of the formula (I) to the compound a is from 1:150 to 3:1.

The present invention further provides a method for controlling pests, which comprises applying the pesticidal composition of the present invention to the pests. The concentrations of the active ingredients in the pesticidal composition of the present invention at the time of application vary depending upon the crop plant as the object, the way of application, the form of a formulation, the dose, the application season and the type of noxious fungi, and hence can not be generically determined. However, in the case of foliage treatment, the concentration of the compound of the formula (I) as the active ingredient is generally from 0.01 to 1,000 ppm, preferably from 0.3 to 500 ppm, and the concentration of said at least one fungicide selected from the group consisting of the compounds a, b, c and d, as the active ingredient, is generally from 0.01 to 1,000 ppm, preferably from 0.5 to 500 ppm.

BEST MODE FOR CARRYING OUT THE INVENTION

Now, examples of preferred embodiments of the pesticidal composition of the present invention are described below. However, the present invention is by no means restricted thereto.

(1) A pesticidal composition comprising at least one compound of the formula (I) and (S)-5-methyl-2-methylthio-S-phenyl-3-phenylamino-3,5-dihydroimidazole-4-one as active ingredients.

(2) The pesticidal composition of item (1), wherein the weight ratio of said at least one compound of the formula (I) to (s)-5-methyl-2-methylthio-5-phenyl-3-phenylamino-3,5-dihydroimidazole-4-one is from 1:1000 to 10000:1.

(3) The pesticidal composition of item (1), wherein the weight ratio of said at least one compound of the formula (I) to (S)-5-methyl-2-methylthio-5-phenyl-3-phenylamino-3,5-dihydroimidazole-4-one is from 1:200 to 200:1.

(4) The pesticidal composition of item (1), wherein the weight ratio of said at least one compound of the formula (I) to (S)-5-methyl-2-methylthio-5-phenyl-3-phenylamino-3,5-dihydroimidazole-4-one is from 1:150 to 3:1.

(5) A pesticidal composition comprising at least one compound of the formula (I) and isopropyl 2-methyl-1-[(1-p-tolylethyl)carbamoyl]-(S)-propylcarbamate as active ingredients.

(6) A pesticidal composition comprising at least one compound of the formula (I) and 3,5-dichloro-N-(3-chloro-1-ethyl-1-methyl-2-oxopropyl)-4-methylbenzamide as active ingredients.

(7) A pesticidal composition comprising at least one compound of the formula (I) and N-(a-cyano-2-thienyl)-4-ethyl-2-(ethylamino)-5-thiazole carboxyamide as active ingredients.

Now, Test Examples of the present invention will be described below. However, the present invention is by no means restricted thereto.

TEST EXAMPLE 1

Test on Preventive Effect Against Cucumber Downy Mildew

Cucumber (cultivar: Suyo) was cultivated in a polyethylene pot having a diameter of 7.5 cm, and when the cucumber reached a two-leaf stage, two seedlings of the cucumber were sprayed with a drug solution having predetermined concentrations of sample compounds in an amount of 1,000 l/ha by a spray gun. On the next day after the treatment, the cucumber was sprayed and inoculated with a zoosporangia suspension of fungi of cucumber downy mildew, and the cucumber was kept in a moist chamber at 20° C. for 18 hours. Then, it was kept in a constant temperature chamber of 20° C. for from 6 to 7 days, and the average area of lesions on the first leaves of the two seedlings was examined to find the incidence according to the following formula. Here, the average area of lesions in the non-treated plot was obtained in the same manner as the treated plot, except that the cucumber was sprayed with water instead of the drug solution by a spray gun. The results are shown in Tables 1 to 4.

Incidence=(a/b)×100 a: Average area of lesions in the treated plot
b: Average area of lesions in the non-treated plot Further, the theoretical value can be calculated from the following Colby's formula:

Theoretical value=(X×Y)/100

X: Incidence (%) in the case of treatment with the compound No. 1 alone
Y: Incidence (%) in the case of treatment with the compound a, b, c or d alone When the experimental values are lower than the theoretical values by Colby's formula, the pesticidal composition of the present invention has a synergistic effect of controlling pests. The theoretical values by Colby's formula in such cases are shown in parenthesis ( ) in Tables 1 to 4.

TABLE 1

Compd. No. 1
Incidence of cucumber downy mildew
(theoretical value)

| Compd. a | 0.25 ppm | 0.125 ppm | 0.062 ppm | 0 ppm |
|---|---|---|---|---|
| 1 ppm | 2.6 | 0 (2.6) | 7.7 (10.8) | 12.8 |
| 0.5 ppm | 0 (3.4) | 2.6 (13.7) | 23.1 (56.4) | 66.7 |
| 0.25 ppm | 2.6 (4.2) | 30.8 | 61.5 (69.4) | 82.1 |
| 0 ppm | 5.1 | 20.5 | 87.6 | |

TABLE 2

Compd. No. 1
Incidence of cucumber downy mildew
(theoretical value)

| Compd. b | 0.125 ppm | 0.062 ppm | 0 ppm |
|---|---|---|---|
| 16 ppm | 5.2 (8.8) | 30.9 | 15.5 |
| 8 ppm | 10.3 (26.3) | 56.7 | 46.4 |
| 4 ppm | 25.8 (38.0) | 51.5 (58.7) | 67.0 |
| 2 ppm | 30.9 (49.7) | 92.8 | 87.6 |
| 0 ppm | 56.7 | 84.6 | |

TABLE 3

Compd. No. 1
Incidence of cucumber downy mildew
(theoretical value)

| Compd. c | 0.25 ppm | 0.125 ppm | 0.062 ppm | 0 ppm |
|---|---|---|---|---|
| 2 ppm | 5.1 | 0 (1.6) | 35.6 | 61.0 |
| 1 ppm | 0 (1.8) | 0 (1.8) | 15.3 (18.1) | 71.2 |
| 0.5 ppm | 0 (2.4) | 2.5 | 15.3 (24.4) | 95.8 |
| 0 ppm | 2.5 | 2.5 | 25.4 | |

TABLE 4

Compd. No. 1
Incidence of cucumber downy mildew
(theoretical value)

| Compd. d | 1 ppm | 0.5 ppm | 0.25 ppm | 0.06 ppm | 0 ppm |
|---|---|---|---|---|---|
| 16 ppm | 0 | 0 (0.5) | 0 (1.0) | 7.5 (17.0) | 20 |
| 8 ppm | 0 | 0 (0.38) | 0 (0.75) | 7.5 (12.8) | 15 |
| 1 ppm | 0 | 0 (2.5) | 2.5 (5.0) | 80 (85) | 100 |
| 0 ppm | 0 | 2.5 | 5.0 | 85 | |

TEST EXAMPLE 2

Test on Preventive Effect Against Tomato Late Blight

Tomato (cultivar: Ponderosa) was cultivated in a polyethylene pot having a diameter of 7.5 cm, and when the tomato reached a four-leaf stage, two seedlings of the tomato were sprayed with a drug solution having predetermined concentrations of sample compounds in an amount of 1,000 l/ha by a spray gun. On the next day after the treatment, the tomato was sprayed and inoculated with a zoosporangia suspension of fungi of tomato late blight, and the tomato was kept in a moist chamber at 20° C. for 18 hours. Then, it was kept in a constant temperature chamber of 20° C. for 3 days, and the degree of disease outbreak of leaves was examined as described below, to find the degree of disease from the following formula:

Decree of Disease Outbreak

0: No lesions were recognizable
1. Lesions were slightly recognizable

2: Area of lesions is less than 25% of the area of leaves

3: Area of lesions is at least 25% and less than 50% of the area of leaves

4: Area of lesions is not smaller than 50% of the area of leaves

Degree of disease=[(0×A+1×B+2×C+3×D+4×E)/(4×(A+B+C+D+E))]×100

A: Number of leaves with degree of disease outbreak of 0
B: Number of leaves with degree of disease outbreak of 1
C: Number of leaves with degree of disease outbreak of 2
D: Number of leaves with degree of disease outbreak of 3
E: Number of leaves with degree of disease outbreak of 4

Further, using the average degree of disease of two seedlings, the incidence was calculated from the following formula, and the results are shown in Tables 5 to 8. Here, the average degree of disease of the non-treated plot was obtained in the same manner as the treated plot, except that the tomato was sprayed with water instead of the drug solution by a spray gun.

Incidence=(a'/b')×100 a': Average degree of disease of treated plot
b': Average degree of disease of non-treated plot Further, a theoretical value can be calculated from the following Colby's formula. When the experimental values are lower than the theoretical values by Colby's formula, the pesticidal composition of the present invention has a synergistic effect of controlling pests. Theoretical values by the Colby's formula in such cases are shown in parenthesis ( ) in Tables 5 to 8.

Theoretical value=(X'×Y')/100

X': Incidence (%) in the case of treatment with the compound No. 1 alone
Y': Incidence (%) in the case of treatment with the compound a, b, c or d alone

TABLE 5

| | Compd. No. 1 Incidence of tomato late blight (theoretical value) | | | |
|---|---|---|---|---|
| Compd. a | 0.25 ppm | 1.125 ppm | 0.062 ppm | 0 ppm |
| 1 ppm | 3.2 (13.7) | 18.9 (37.0) | 25.2 (48.8) | 53.5 |
| 0.5 ppm | 6.3 (16.9) | 22.0 (45.7) | 44.1 (60.3) | 66.1 |
| 0.25 ppm | 25.2 | 31.5 (65.4) | 56.6 (86.1) | 94.4 |
| 0.125 ppm | 31.5 | 31.5 (67.3) | 81.8 (88.7) | 97.2 |
| 0.062 ppm | 34.6 | 53.5 (69.2) | 66.1 (91.3) | 100 |
| 0 ppm | 25.6 | 69.2 | 91.3 | |

TABLE 6

| | Compd. No. 1 Incidence of tomato late blight (theoretical value) | | | | |
|---|---|---|---|---|---|
| Compd. b | 0.50 ppm | 0.25 ppm | 1.125 ppm | 0.062 ppm | 0 ppm |
| 8 ppm | 18.8 (23.4) | 15.6 (36.6) | 31.3 (41.0) | 34.4 (42.5) | 46.9 |
| 4 ppm | 18.8 (35.9) | 46.9 (56.2) | 56.3 (62.9) | 56.3 (65.1) | 71.9 |

TABLE 6-continued

| | Compd. No. 1 Incidence of tomato late blight (theoretical value) | | | | |
|---|---|---|---|---|---|
| Compd. b | 0.50 ppm | 0.25 ppm | 1.125 ppm | 0.062 ppm | 0 ppm |
| 1 ppm | 28.1 (50.0) | 75.0 (78.1) | 87.5 (87.5) | 87.5 (90.6) | 100 |
| 0 ppm | 50.0 | 78.1 | 87.5 | 90.6 | |

TABLE 7

| | Compd. No. 1 Incidence of tomato late blight (theoretical value) | | | | |
|---|---|---|---|---|---|
| Compd. c | 0.50 ppm | 0.25 ppm | 0.125 ppm | 0.062 ppm | 0 ppm |
| 8 ppm | 0 (2.0) | 3.1 (6.8) | 6.3 (11.7) | 9.4 (20.5) | 31.3 |
| 4 ppm | 0 (3.9) | 12.5 (13.7) | 28.1 | 28.1 (41.0) | 62.5 |
| 1 ppm | 0 (3.9) | 6.3 (13.7) | 18.8 (23.4) | 37.5 (41.0) | 62.5 |
| 0 ppm | 6.3 | 21.9 | 37.5 | 65.6 | |

TABLE 8

| | Compd. No. 1 Incidence of tomato late blight (theoretical value) | | | |
|---|---|---|---|---|
| Compd. d | 0.5 ppm | 0.25 ppm | 0.125 ppm | 0 ppm |
| 16 ppm | 0 | 4.2 (16.5) | 12.5 (16.5) | 16.5 |
| 8 ppm | 12.5 | 25 (29.2) | 25 (29.2) | 29.2 |
| 4 ppm | 20.9 | 41.7 (75) | 54.2 (75) | 75 |
| 0 ppm | 83.4 | 100 | 100 | |

Now, the Formulation Examples of the pesticidal composition of the present invention will be described below. However, the present invention is by no means restricted thereto.

FORMULATION EXAMPLE 1

| (i) Kaoline | 78 parts by weight |
| (ii) Sodium β-naphthalenesulfonate formalin condensate | 2 parts by weight |
| (iii) Polyoxyethylenealkylaryl sulfate | 5 parts by weight |
| (iv) Hydrated amorphous silicon dioxide | 15 parts by weight |

A mixture of the above components, the compound No. 1 and the compound a are mixed in a weight ratio of 8:1:1 to obtain a wettable powder.

FORMULATION EXAMPLE 2

| (i) Compound No. 1 | 0.5 part by weight |
| (ii) Compound a | 0.5 part by weight |
| (iii) Bentonite | 20 parts by weight |
| (iv) Kaoline | 74 parts by weight |
| (v) Sodium lignin sulfonate | 5 parts by weight |

To the above components, water required for granulation was added in an appropriate amount, followed by mixing and granulation to obtain granules.

FORMULATION EXAMPLE 3

| | |
|---|---|
| (i) Compound No. 1 | 0.25 part by weight |
| (ii) Compound a | 0.25 part by weight |
| (iii) Calcium carbonate | 99.0 parts by weight |
| (iv) Lower alcohol phosphate | 0.5 part by weight |

The above components are uniformly mixed to obtain a dust.

INDUSTRIAL APPLICABILITY

The pesticidal composition of the present invention has a stable and high effect of controlling pests over crop plants which suffer from plant diseases caused by pests, and the pests can be controlled by using said composition.

What is claimed is:

1. A pesticidal composition comprising at least one imidazole compound of the formula (I):

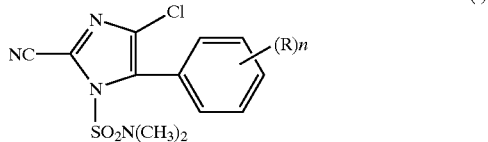

formula (I)

wherein R is a lower alkyl group or a lower alkoxy group, and n is an integer of from 1 to 5, and at least one fungicide selected from the group consisting of (S)-5-methyl-2-methylthio-5-phenyl-3-phenylamino-3,5-dihydroimidazole-4-one, isopropyl 2-methyl-1-[(1-p-tolylethyl)carbamoyl]-(S)-propylcarbamate, 3,5-dichloro-N-(3-chloro-1-ethyl-1-methyl-2-oxopropyl)-4-methylbenzamide and N-(α-cyano-2-thienyl)-4-ethyl-2-(ethylamino)-5-thiazole carboxyamide, as active ingredients.

2. The pesticidal composition according to claim 1, wherein the weight ratio of the imidazole compound of the formula (I) to said at least one fungicide selected from the group consisting of (S)-5-methyl-2-methylthio-5-phenyl-3-phenylamino-3,5-dihydroimidazole-4-one, isopropyl 2-methyl-1-[(1-p-tolylethyl)carbamoyl]-(S)-propylcarbamate, 3,5-dichloro-N-(3-chloro-1-ethyl-1-methyl-2-oxopropyl)-4-methylbenzamide and N-(α-cyano-2-thienyl)-4-ethyl-2-(ethylamino)-5-thiazole carboxyamide, is from 1:10,000 to 10,000:1.

3. A method for controlling pests, which comprises applying the pesticidal composition as defined in claim 1 to the pests.

4. A method for controlling pests, which comprises applying the pesticidal composition as defined in claim 2 to the pests.

5. A pesticidal composition according to claim 2 wherein the fungicide is fungicide (A).

6. A pesticidal composition according to claim 2 wherein the fungicide is fungicide (B).

7. A pesticidal composition according to claim 2 wherein the fungicide is fungicide (C).

* * * * *